(12) United States Patent
Romagnano et al.

(10) Patent No.: US 7,868,054 B2
(45) Date of Patent: Jan. 11, 2011

(54) PHENYLGLYOXALIC ESTERS GENERATED BY PHOTOLYSIS OF LOW MIGRATABLE FRAGMENTS

(75) Inventors: Stefano Romagnano, Lainate (IT); Gabriele Norcini, Comabbio (IT); Marco Visconti, Varese (IT); Giuseppe Libassi, Gavirate (IT)

(73) Assignee: Lamberti SpA, Albizzate (IT)

( * ) Notice: Subject to any disclaimer, the term of this patent is extended or adjusted under 35 U.S.C. 154(b) by 555 days.

(21) Appl. No.: 11/914,245

(22) PCT Filed: May 10, 2006

(86) PCT No.: PCT/EP2006/062206
§ 371 (c)(1),
(2), (4) Date: Nov. 13, 2007

(87) PCT Pub. No.: WO2006/120212
PCT Pub. Date: Nov. 16, 2006

(65) Prior Publication Data
US 2008/0193677 A1     Aug. 14, 2008

(30) Foreign Application Priority Data
May 13, 2005   (IT) .................... VA2005A0032

(51) Int. Cl.
C08F 2/50 (2006.01)
C08J 3/28 (2006.01)

(52) U.S. Cl. .............. 522/36; 522/70; 522/33; 522/113; 522/116; 522/120; 522/173; 522/178; 522/182; 522/909; 568/397; 568/410; 568/336; 427/508; 427/510; 427/511; 427/517; 427/520

(58) Field of Classification Search .......... 522/36, 522/33, 70, 113, 116, 120, 173, 178, 180, 522/909; 568/397, 410, 336; 427/508, 510, 427/511, 517, 520
See application file for complete search history.

(56) References Cited

U.S. PATENT DOCUMENTS

| | | | | |
|---|---|---|---|---|
| 3,844,916 A | * | 10/1974 | Gaske | 522/33 |
| 3,930,868 A | * | 1/1976 | Muzyczko et al. | 430/281.1 |
| 4,038,164 A | | 7/1977 | Via | |
| 4,048,034 A | * | 9/1977 | Martan | 522/39 |
| 4,279,718 A | * | 7/1981 | Schuster et al. | 522/34 |
| 4,315,791 A | * | 2/1982 | Ishii et al. | 156/304.2 |
| 4,321,118 A | * | 3/1982 | Felder et al. | 522/36 |
| 4,475,999 A | * | 10/1984 | Via | 522/20 |
| 4,987,159 A | * | 1/1991 | Li Bassi et al. | 522/36 |
| 6,562,464 B1 | * | 5/2003 | Schwalm et al. | 428/411.1 |
| 7,105,582 B2 | * | 9/2006 | Baudin et al. | 522/35 |
| 7,309,550 B2 | * | 12/2007 | Rach et al. | 430/18 |
| 7,723,397 B2 | * | 5/2010 | Husler et al. | 522/36 |
| 2005/0004249 A1 | * | 1/2005 | Fuchs et al. | 522/36 |

FOREIGN PATENT DOCUMENTS

WO    WO 2004009651 A1 *  1/2004

OTHER PUBLICATIONS

Labadie; Linear Poly(quinoxalones); Macomolecules (1989) 22, pp. 1507-1509.*
Labadie, Jeff W. Poly(quinoxalones): Synthesis and Properties. Polymeric Materials Science and Engineering (1988), 59, pp. 37-41.*
Labadie, Jeff W. Poly (Quinoxalones). POlymeric Materials Science and Engineering. (1989), 60, pp. 532-532.*
Yamazaki et al. Photochemical Dimerization of Benzoselenete Derivative. Journal of Organic Chemistry. (1989), 54, pp. 240-243.*
Wallraff et al. Synthesis and Lithograpic Performance of Photosensitive Poly (phenylquinoxaline)s and Related Structures. Polymeric Materials Sciences and Engineering (1992), 66, pp. 289-290.*

* cited by examiner

*Primary Examiner*—Sanza L McClendon
(74) *Attorney, Agent, or Firm*—Mossman, Kumar & Tyler, PC

(57) ABSTRACT

The present invention concerns photopolymerisable systems comprising reactive oligomers and/or monomers having ethylenically unsaturated groups and at least one phenylglyoxalic ester that, by photochemical decomposition, generates fragments having low migratability and low odor.

20 Claims, No Drawings

PHENYLGLYOXALIC ESTERS GENERATED BY PHOTOLYSIS OF LOW MIGRATABLE FRAGMENTS

This application is a 371 of international application PCT/EP2006/062206, filed on May 10, 2006.

This invention concerns photopolymerisable systems containing phenylglyoxalic esters that, by photochemical decomposition, generate fragments having low migratability and low odour.

Photopolymerisable systems contain photoinitiators characterised by the presence within their molecule of a functional group that, by electromagnetic excitation, generally UV radiation, generates radicals that are able to start a polymerisation process.

As it is known, both the photoinitiators and the fragments deriving from photochemical decomposition during the polymerisation process must follow strict criteria of low toxicity, volatility, migratability and odour and must be highly compatible within the photopolymerisable system.

These characteristics are essential particularly in the field of food packaging coating.

Aromatic phenylglyoxalic esters and their use as photoinitiators are known and described, for example, in U.S. Pat. No. 4,038,164, U.S. Pat. No. 4,024,297 and U.S. Pat. No. 4,475,999.

More recently, in U.S. Pat. No. 6,048,660, a large family of phenylglyoxalic esters is described; they are said to possess low volatility and low odour, but it is not reported if such characteristics can also be found in the products originating from their photo-decomposition.

The products originating from the decomposition of the phenylglyoxalic esters of U.S. Pat. No. 6,048,660, nonetheless, derive from the radicals $R_1CO$ and $R_2CO$; in the simplest cases, these radicals become benzaldehyde, 4-methoxy-benzaldehyde, 4-methylthio-benzaldehyde, etc. . . . which are notoriously irritant and malodorous.

We have now found that the members of a restricted family of aromatic phenylglyoxalic esters having formula I:

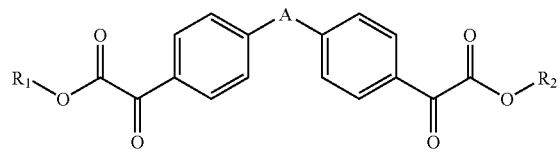

I wherein

A is selected among O, S, $NR_3$, linear or branched $C_1$-$C_6$ alkyl or cycloalkyl and $R_3$ is hydrogen or $C_1$-$C_6$ linear or branched alkyl;

$R_1$ and $R_2$ are, independently of one another, linear or branched $C_1$-$C_{18}$ alkyl or cycloalkyl, $(CH_2CH_2O)_nR_4$ where n is a number from 1 to 6 and $R_4$ is hydrogen or linear or branched $C_1$-$C_4$ alkyl, or $CH_2CH_2N(R_5)_2$ where $R_5$ is linear or branched $C_1$-$C_4$ alkyl, by photochemical decomposition, generate fragments having low migratability, volatility and odour.

The photopolymerisable systems comprising reactive oligomers and/or monomers having ethylenically unsaturated groups and, as photoinitiators, the phenylglyoxalic esters of formula I are a fundamental object of the present invention, and are particularly useful for the preparation of coatings for food packaging.

Among the products which are particularly useful for the realisation of the present invention we cite the compounds of formula I wherein A is selected among O, S or $CH_2$, and $R_1$ and $R_2$ are methyl, ethyl, i-propyl, n-propyl, n-butyl, i-butyl, t-butyl, or $CH_2CH_2OR_4$ where $R_4$ is hydrogen, methyl or ethyl; the preferred products are those having formula Ia-Ie:

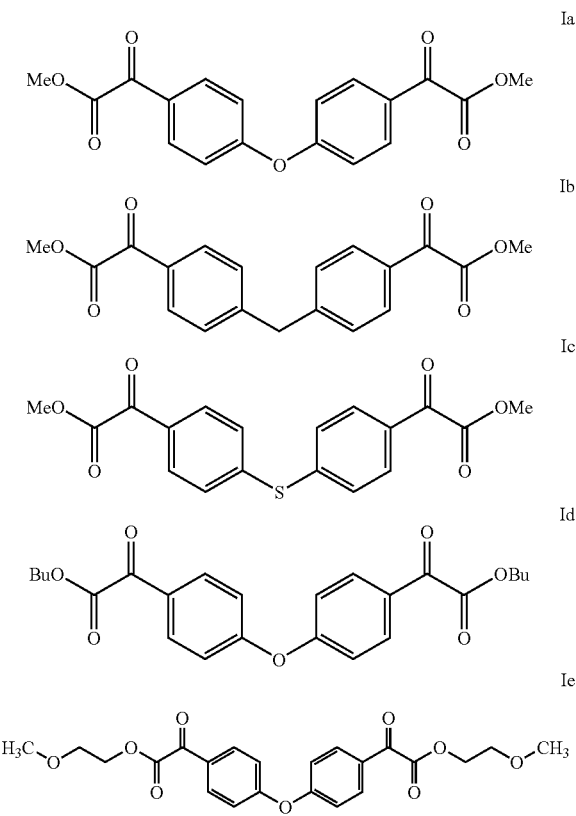

The phenylglyoxalic esters of formula I of the present invention may be prepared by conventional methods which are well known to the man skilled in the art.

In particular, it is possible to carry out a Friedel Crafts reaction between

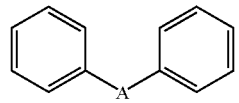

where A is selected among O, S, $NR_3$, linear or branched $C_1$-$C_6$ alkyl or cycloalkyl and $R_3$ is hydrogen or linear or branched $C_2$-$C_6$ alkyl, and methyl oxalyl chloride and optionally transesterifiying the obtained product with $R_1OH$ and/or $R_2OH$, where $R_1$ and $R_2$ are, independently of one another, linear or branched $C_2$-$C_{18}$ alkyl or cycloalkyl, $(CH_2CH_2O)_n R_4$ where n is a number from 1 to 6 and $R_4$ is hydrogen or linear or branched $C_1$-$C_4$ alkyl, or $CH_2CH_2N(R_5)_2$ where $R_5$ is linear or branched $C_1$-$C_4$ alkyl, in the presence of a transesterification catalyst.

It is a further object of the present invention a process for the realisation of coatings for metal, wood, paper or plastic surfaces, comprising applying the photopolymerisable system comprising reactive oligomers and/or monomers having ethylenically unsaturated groups and at least one phenylglyoxalic esters of formula I, and preferably of formula Ia, Ib, Ic, Id, or Ie, to obtain, after polymerisation, a 0.5 to 100 microns thick coating, and subsequently photopolymerising with a light source having emission bands in the UV-visible region and up to 450 nm.

The term "photopolymerisation" is intended in a wide sense and include, for example, the polymerisation or crosslinking of polymeric materials, such as for example pre-polymers, the homopolymerisation and the copolymerisation of simple monomers and the combination of this kind of reactions.

Monomers useful in the described system include, for example: acrylonitrile, acrylamide and its derivatives, vinyl ethers, N-vinylpyrrolidone, mono and polyfunctional allyl ethers, such as for example trimethylolpropane diallylether, styrenes and alpha-methyl styrenes, esters of acrylic and methacrylic acid with alyphatic alcohols, with glycols, or with polyhydroxylated compounds, as for example pentaerythritol, trimethylolpropane or aminoalcohols, esters of vinyl alcohol with aliphatic or acrylic acids, derivatives of fumaric or maleic acid.

The oligomers which are useful for the present invention include, for example, polyesters, polyacrylates, polyurethanes, epoxidic resins, polyethers with acrylic, maleic or fumaric functionalities.

Compounds of formula I of the present invention acts as photoinitiators and can be used alone or in combination with other photoinitiators as for example benzophenone and its derivatives (such as methylbenzophenone, trimethylbenzophenone), acetophenone derivatives, such as for example α-hydroxyacetophenones, (as α-hydroxycyclohexylphenyl ketone, oligo-[2-hydroxy-2-methyl-1-[4-(1-methylvinyl)phenyl]-propanone], 2-hydroxy-2-methyl-1-phenyl-propanone, 2-hydroxy-1-[4-(2-hydroxy-ethoxy)-phenyl]-2-methyl-propan-1-one, 1-[2,3-dihydro-1-[4-(2-hydroxy-2-methyl-1-oxopropyl)phenyl]-1,3,3-trimethyl-1H-inden-5-yl]-2-hydroxy-2-methyl-1-propanone, 1-[2,3-dihydro-3-[4-(2-hydroxy-2-methyl-1-oxopropyl)phenyl]-1,1,3-trimethyl-1H-inden-5-il]-2-hydroxy-2-methyl-1-propanone, 4,3'-bis(α,α-hydroxy-isobutyryl)-diphenylmethane, 4,4'-bis(α,α-hydroxy-isobutyryl)-diphenylmethane, 4,3'-bis(α,α-hydroxy-isobutyryl)-diphenylether, 4,4'-bis(α,α-hydroxy-isobutyryl)-diphenylether), α-aminoacetophenones (as 2-dimethylamino-2-(4-methylbenzyl)-1-(4-morpholin-4-yl-phenyl)-butan-1-one, 2-benzyl-2-dimethylamino-1-(3,4-dimethoxy-phenyl)-butan-1-one, 2-benzyl-2-dimethylamino-1-(4-morpholin-4-yl-phenyl)-butan-1-one, 2-methyl-1-(4-methylsulfanyl-phenyl)-2-morpholin-4-yl-propan-1-one), ketosulfones (as 1-[4-(4-benzoyl-phenylsulfanyl)-phenyl]-2-methyl-2-(toluene-4-sulfonyl)-propan-1-one), dialcoxyacetophenones, benzoin ethers, benzyl ketals (as benzyl dimethyl ketal), phenylglyoxylic acid esters and their derivatives (as phenylglyoxylic acid methyl ester, ethyl ester of 2-(2-oxo-2-phenyl-acetoxy-etoxyethyl)oxyphenylacetic acid), monoacylphosphine oxides, as (2,4,6-trimethylbenzoyl)-diphenyl-phosphine oxide or the ethyl ester of phenyl-(2,4,6-trimethylbenzoyl)-phosphinic acid, bisacylphosphine oxides, (as bis-(2,6-dimethoxybenzoyl)-(2,4,4-trimethyl-pent-1-yl)phosphine oxide, bis(2,4,6-trimethyl benzoyl)-phenyl-phosphine oxide, bis(2,4,6-trimethylbenzoyl)-(2,4-dipentoxyphenyl)phosphine oxide), trisacylphosphine oxides, halogenomethyltriazine, ferrocene or titanocene derivatives, photoinitiators containing the borate or O-acyloximic group, sulphonium, phosphonium or iodonium aromatic salts.

In addition to the compounds of formula I, many other components may be included in the photopolymerisable systems of the invention, for example thermal stabilisers, sensitisers, photo-oxydation stabilisers such as sterically hindered amines, antioxidants, oxygen inhibitors, thermal radicals generators such as organic and inorganic peroxides, peresters, hydroperoxides, benzopinacols, azoderivatives such as azodiisobutyronitrile, metallic compounds such as cobalt(II) salts, manganese, antifoams, fillers, dispersing agents, pigments, dyes and/or matting agents, other additives of general use, dispersed solids, glass and carbon fibres, thixotropic agents.

Chemically inert non photopolymerisable polymers, as for example nitrocellulose, polyacrylic esters, polyolefines etc., or polymers which are crosslinkables with other systems, as for example with peroxides and atmospheric oxygen or acid catalysis or thermal activation, as for example polyisocyanates, urea, melamine or epoxidic resins are further components that may be included in the photopolymerisable systems.

The compounds of formula I are generally used in the photopolymerisable system in quantity of 0.01 to 20% by weight, preferably of 1 to 6% by weight, on the total weight of the photopolymerisable system and are perfectly compatible with the system, imparting to it high photochemical reactivity and heat stability.

The compounds of formula I are very efficient photoinitiators both in clear and in pigmented photopolymerisable systems and are useful for example for the preparation of photocrosslinkable inks. They are especially suited for use in the coating of PVC floor and in the automobile field.

Examples of sources of light useful for the photopolymerisation of the photopolymerisable systems prepared according to the invention are mercury vapour or superactinic or excimers lamps, with emission bands in the UV-visible region and particularly between 180 and 450 nm.

Among the useful sources of light, sunlight and other artificial sources emitting electromagnetic radiation with a wavelength from 180 nm up to the IR region are also included.

A further advantage of the present invention is the fact that, using starting compounds which are easily available on the market, by varying the group A in formula I, it is possible to modify the absorbance spectrum of the phenylglyoxalic ester so to increase its reactivity in pigmented systems.

The phenylglyoxalic esters of the present invention have a high reactivity, as shown in the application tests here reported; beside not generating benzaldehyde or substituted benzaldehyde, they are themselves low migratable, low volatile and low odorous.

Examples of the preparation of compounds of formula I and of photopolymerisable systems containing them are herein reported, not to limit but to illustrate the invention.

EXAMPLE 1

Synthesis of [4-(4-Methoxyoxalyl-phenoxy)-phenyl]-oxo-acetic acid methyl ester (Ia)

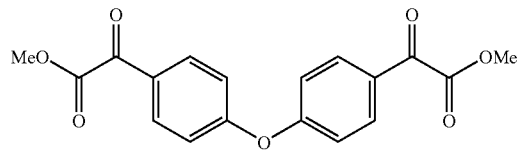

31.3 g (0.235 mol) of AlCl$_3$ were added in 30', under stirring and in portions, to a solution of 10 g (0.0587 mol) of diphenylether and 11.33 ml (0.123 mol) of methyl oxalyl chloride in 300 ml of dichloromethane, at a temperature of 0 to 5° C.

At the end of the addition the temperature was raised to room temperature and after three hours the reaction was completed. The reaction mixture was poured into a solution of 200 ml of water and ice acidified with 15 ml of concentrated HCl. The organic phase was separated, washed twice with brine, dried on sodium sulphate, and evaporated under vacuum. The oily residue, taken with 100 ml of petroleum ether, solidified. 17.4 g of product Ia were obtained (yield 87%).

$^1$HNMR, 300 MHz, CDCl$_3$ δ(ppm): 8.10, m, 4H; 7.12, m, 4H; 3.98, s, 6H

EXAMPLE 2

Synthesis of
[4-(4-Methoxyoxalyl-benzyl)-phenyl]-oxo-acetic acid methyl ester (Ib)

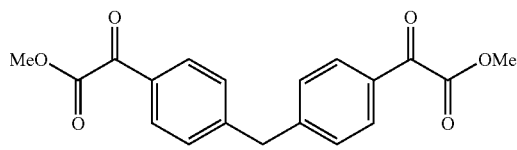

5.33 g (0.04 mol) of AlCl$_3$ were added in one portion, under stirring at room temperature, to a solution of 1.68 g (0.01 mol) of diphenylmethane and 1.93 ml (0.021 mol) of methyl oxalyl chloride in 100 ml of dichloromethane.

After four hours the reaction was completed. The reaction mixture was poured into a solution of 100 ml of water and ice acidified with 2.5 ml of conc. HCl. The organic phase was separated, washed twice with brine, dried on sodium sulphate, and evaporated under vacuum. The oily residue was washed with petroleum ether and then evaporated.

3.2 g of product Ib were obtained as a yellow oil (yield 94%).

$^1$H-NMR, 300 MHz, CDCl$_3$ δ(ppm): 8.10, m, 4H; 7.32, m, 4H; 4.15, s, 2H; 3.98, s, 6H

EXAMPLE 3

Synthesis of [4-(4-Methoxyoxalyl-phenylsulfanyl)-phenyl]-oxo-acetic acid methyl ester (Ic)

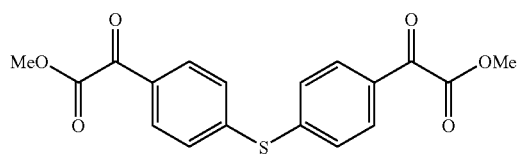

7.14 g (0.0536 mol) of AlCl$_3$ were added in one portion, under stirring at room temperature, to a solution of 2.5 g (0.0134 mol) of diphenylsulphide and 2.58 ml (0.0281 mol) of methyl oxalyl chloride in 100 ml of dichloromethane. A sticky precipitated product was formed.

100 ml of dichloromethane were added and the mixture was left overnight at r.t.

The reaction mixture was poured into a solution of 200 ml of water and ice acidified with 3.5 ml of conc. HCl. The organic phase was separated, washed twice with brine, dried on sodium sulphate, and evaporated under vacuum. The oily residue was washed with petroleum ether and then evaporated.

5 g of product were obtained as an oil.

The product was purified by flash chromatography eluting with dichloromethane/petroleum ether 7/3 and then with dichloromethane.

The residue solidified in petroleum ether and was filtrated; 850 mg of product Ic were obtained.

$^1$H-NMR, 300 MHz, CDCl$_3$ δppm): 8.01, m, 4H; 7.49, m, 4H; 3.98, s, 6H.

EXAMPLE 4

Synthesis of
[4-(4-Butoxyoxalyl-phenoxy)-phenyl]-oxo-acetic acid butyl ester (Id)

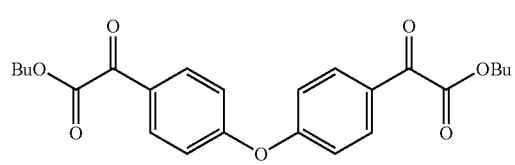

50.5 mg (0.2 mmol) of dibutyltin oxide were added to a suspension of 2 g of product Ia in 10 ml of n-butanol. The reaction was heated under reflux and a solution obtained. After two hours the reaction was completed. The solution was diluted with 100 ml of dichloromethane and the organic phase washed twice with water, dried on sodium sulphate, and evaporated under vacuum to give an oily product which was purified by flash chromatography eluting with petroleum ether/dichloromethane 1/1.

1.6 g of product Id were obtained as a yellow oil.

$^1$H-NMR, 300 MHz, CDCl$_3$ δ(ppm): 8.1, m, 4H; 7.15, m, 4H; 4.4, t, 4H; 1.78, m, 4H; 1.45, m, 4H; 0.9, t, 6H

EXAMPLE 5

Synthesis of {4-[4-(2-Methoxy-ethoxyoxalyl)-phenoxy]-phenyl}-oxo-acetic acid 2-methoxy-ethyl ester (Ie)

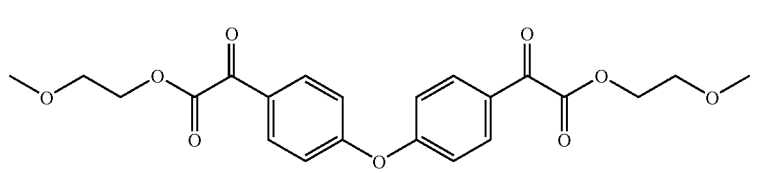

50.5 mg (0.2 mmol) of dibutyltin oxide were added to a suspension of 2 g of product Ia in 10 ml of 2-methoxyethanol. The reaction was heated under reflux and a solution obtained. After two hours the reaction was completed. The solution was diluted with 100 ml of dichloromethane and the organic phase washed twice with water, dried on sodium sulphate, and evaporated under vacuum to give an oily product which was purified by flash chromatography eluting with petroleum ether/ethyl acetate 6/4.

730 mg of product Ie were obtained as a yellowish oil.

$^1$H-NMR, 300 MHz, CDCl$_3$ δ(ppm):): 8.1, m, 4H; 7.15, m, 4H; 4.55 μm, 4H; 3.73, m, 4H; 3.41, s, 6H.

Application Tests.

The substances used for the preparation of the photopolymerisable systems evaluated in the following applicative tests are:

Ebecryl (R)284 (aliphatic urethane acrylate from UCB, Belgium);

TPGDA (tripropylene glycol diacrylate)

TMPTA (trimethylolpropane triacrylate).

As photoinitiators, the compounds Ia-Ie of Examples 1-5 were used:

For the evaluation of the photopolymerisable systems, two matrixes were prepared mixing (% w/w), for the first matrix M1:

| Ebecryl 284 (R) | 70% |
| TMPTA | 15% |
| TPGDA | 15% | for the second matrix M2:

| Ebecryl 284 (R) | 75% |
| TPGDA | 25% |

The photopolymerisable systems to be evaluated are then prepared with the compositions reported in Table 1.

TABLE 1

Photopolymerisable systems composition (% w/w)

|  | A | B | C | D | E | F |
|---|---|---|---|---|---|---|
| Matrix M1 | 95 | | | | | |
| Matrix M2 | | 96 | 96 | 96 | 96 | 96 |
| Compound Ia | 5 | 4 | | | | |
| Compound Ib | | | 4 | | | |
| Compound Ic | | | | 4 | | |
| Compound Id | | | | | 4 | |
| Compound Ie | | | | | | 4 |

The evaluation of the photopolymerisable systems was done by determining the reactivity, through cure and yellow and white indexes.

Reactivity.

The photopolymerisable system is laid with a thickness of 50 or 6 microns on a varnished cardboard using a bar-coater mounted on an electric stretch-film and thereafter irradiated at a distance of 26 cm from the light source. A Fusion(R) photopolymerisator was used, equipped with a medium pressure mercury lamp operating with about 50% of its nominal power (about 120 W/cm).

The photopolymerisation speed, measured in m/min, is the maximum possible speed that results in a perfect superficial crosslinking of the system ("tack free").

The maximum speed (expressed in m/min) resulting in a surface resistant to any visible damage after rubbing with abrasive paper was also measured (superficial abrasion).

The greater is the maximum speed, the greater is the efficiency of the system.

The obtained results are reported in Table 2.

TABLE 2

|  | A | B | C | E | D | F |
|---|---|---|---|---|---|---|
| Tack-free (m/min) 50 μm | 45 | 41 | 36.5 | 32 | 28 | 27 |
| Tack-free (m/min) 6 μm | 43.5 | — | — | — | — | — |
| Superficial abrasion (m/min) 50 μm | 10 | 10** | 10*** | 10*** | 5 | 4 |

**two passages
***three passages

White and Yellow index

The photopolymerisable system is laid with a thickness of 100 μm on a varnished cardboard using a bar-coater mounted on an electric stretch-film and then is passed at a distance of 26 cm from the light source, at a speed corresponding to 70% of the tack-free speed. A Fusion(R) photopolymerisator was used, equipped with a medium pressure mercury lamp operating with about 50% of its nominal power (about 120 W/cm).

White and yellow indexes were measured according to ASTM D1925-70 standard test method. A low value of yellow index and a high value of white index correspond to high stability of the colour of the formulation.

The results are reported in Table 3.

TABLE 3

|  | A | B | C | E | D | F |
|---|---|---|---|---|---|---|
| Yellow Index | 6.6 | 6.8 | 9.2 | 12.0 | — | — |
| White Index | 66.7 | 66.1 | 60.3 | 53.4 | — | — |

Odour Evaluation.

The photopolymerised systems B-F and a system prepared by mixing 4 parts by weight of Esacure (R)KL200 (hydroxyketone sold by Lamberti SpA) and 96 parts by weight of matrix M2 (photopolymerisable system G) are laid with a thickness of 50 μm on a varnished cardboard using a bar-coater mounted on an electric stretch-film and then is passed at a distance of 26 cm from the light source, at a speed corresponding to 70% of the tack-free speed. A Fusion(R) photopolymerisator was used, equipped with a medium pressure mercury operating with about 50% of its nominal power (about 120 W/cm).

The samples are photopolymerised to obtain a perfect crosslinking ("tack-free").

The thus obtained cardboard samples are put into closed glass jars and the jars are stored in oven for 30 minutes at 60° C.

Three people, independently of one another, evaluate the odour of the samples, rating each photopolymerised system for odour intensity on the following scale:

| No odour | 0 |
| Very slight odour | 1 |
| Slight odour | 2 |

-continued

| | | | | | |
|---|---|---|---|---|---|
| Intense odour | | | 3 | | |
| Very intense odour | | | 4 | | |

The odour evaluations (average of three ratings) are reported in Table 4.

TABLE 4

| | A | B | C | E | D | F |
|---|---|---|---|---|---|---|
| Odour intensity | 1.3 | 2.0 | 2.6 | 1.6 | 1.6 | 3.3 |

The invention claimed is:

1. A photopolymerizable system comprising at least one phenyl glyoxalic ester photoinitiator having the general formula I:

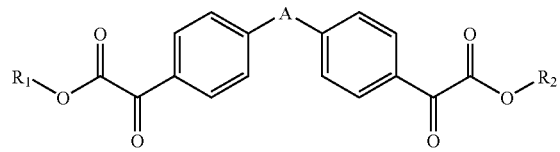

wherein:
A is selected from the group consisting of O, S, NR$_3$, a linear or branched C$_1$-C$_6$ alkyl or cycloalkyl and R$_3$ is hydrogen or a C$_1$-C$_6$ linear or branched alkyl; and
R$_1$ and R$_2$ are, independently of one another, selected from the group consisting of:
a linear or branched C$_1$-C$_{18}$ alkyl or cycloalkyl,
(CH$_2$CH$_2$O)$_n$R$_4$ where n is a integer from 1 to 6 and R$_4$ is hydrogen or a linear or a branched C$_1$-C$_4$ alkyl, and
CH$_2$CH$_2$N(R$_5$)$_2$ where R$_5$ is a linear or branched C$_1$-C$_4$ alkyl.

2. The photopolymerizable system of claim 1 wherein:
A is selected from the group consisting of: O, S or CH$_2$; and
R$_1$ and R$_2$ are, independently of one another, selected from the group consisting of: methyl, ethyl, i-propyl, n-propyl, n-butyl, i-butyl, t-butyl, and CH$_2$CH$_2$OR$_4$ where R$_4$ is hydrogen, methyl or ethyl.

3. The photopolymerizable system of claim 2 wherein the phenyl glyoxalic ester has a formula selected from the group consisting of:

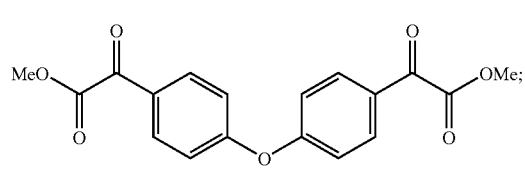

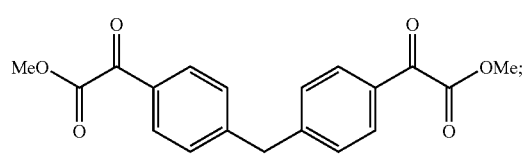

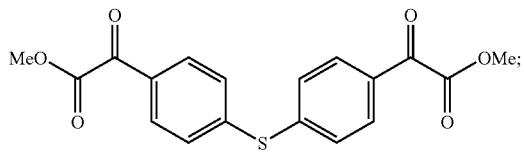

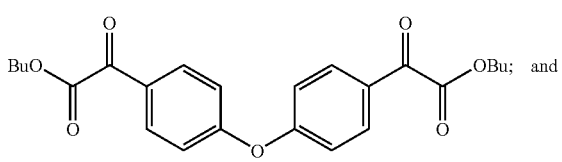

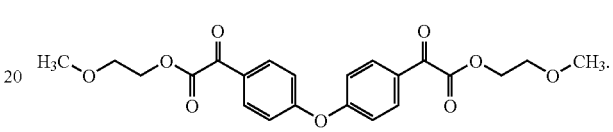

4. The photopolymerizable system of claim 1 further comprising an additional photoinitiator.

5. The photopolymerizable system of claim 4 wherein the additional photoinitiator is a benzophenone photoinitiator.

6. The photopolymerizable system of claim 4 wherein the additional photoinitiator is an α-hydroxyacetophenone photoinitiator.

7. The photopolymerizable system of claim 4 wherein the additional photinitiator is a ketosulfone photoinitiator.

8. The photopolymerizable system of claim 4 wherein the additional photoinitiator is a phenyl glyoxilic acid ester photoinitiator.

9. The photopolymerizable system of claim 4 wherein the additional photoinitiator is selected from the group consisting of acylphosphineoxide photoinitiators; borate photoinitiators; O-acyloximic photoinitiators; sulphonium aromatic salt photoinitiators; phosphonium aromatic salt photoinitiators; iodonium aromatic salt photoinitiators; halogenomethyltriazine photoinitiators; ferrocene photoinitiators; titanocene photoinitiators; and mixtures thereof.

10. The photopolymerizable system of claim 1 additionally comprising at least one member selected from the group consisting of thermal stabilisers, sensitizers, photo-oxidation stabilisers, thermal radicals generators, antifoams, fillers, dispersing agents, pigments, dyes, matting agents, dispersed solids, glass fibers, carbon fibers, thixotropic agents, chemically inert non photopolymerizable polymers, crosslinkable polymers, and mixtures thereof.

11. The photopolymerizable system of claim 1 wherein the phenyl glyoxalic ester is present at a concentration of from about 0.01 to 20 percent by weight.

12. The photopolymerizable system of claim 1 wherein the phenyl glyoxalic ester is present at a concentration of from about 1 to 6 percent by weight.

13. The photopolymerizable system of claim 1 wherein the at least one phenyl glyoxalic ester photoinitiator is prepared using a process including a Friedel Crafts reaction.

14. A process for coating a metal, wood, paper or plastic substrate comprising:
applying to the substrate a photopolymerisable system comprising at least one phenyl glyoxalic ester photoinitiator having the general formula I:

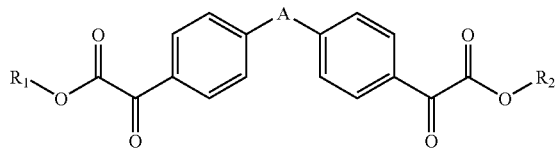

wherein:
- A is selected from the group consisting of O, S, NR₃, a linear or branched $C_1$-$C_6$ alkyl or cycloalkyl and $R_3$ is hydrogen or a $C_1$-$C_6$ linear or branched alkyl; and
- $R_1$ and $R_2$ are, independently of one another, selected from the group consisting of:
- a linear or branched $C_1$-$C_{18}$ alkyl or cycloalkyl,
- $(CH_2CH_2O)_n R_4$ where n is a integer from 1 to 6 and $R_4$ is hydrogen or a linear or a branched $C_1$-$C_4$ alkyl, and
- $CH_2CH_2N(R_5)_2$ where $R_5$ is a linear or branched $C_1$-$C_4$ alkyl;

to obtain, after polymerisation, a coating; and photopolymerising with a light source.

15. The process of claim 14 wherein the coating has a thickness of from about 0.5 to 100 microns and the light source has a emissions in the range of from the UV-visible region to 450 nm.

16. The process of claim 14 wherein A is selected from the group consisting of: O, S or $CH_2$; and $R_1$ and $R_2$ are, independently of one another, selected from the group consisting of: methyl, ethyl, i-propyl, n-propyl, n-butyl, i-butyl, t-butyl, and $CH_2CH_2OR_4$ where $R_4$ is hydrogen, methyl or ethyl.

17. The process of claim 14 wherein the phenyl glyoxalic ester is selected from the group comprising compounds having the formulas Ia, Ib, Ic, Id, and Ie.

18. The process of claim 14 wherein the substrate is suitable for accepting inks and dyes.

19. The process of claim 14 wherein the substrate is a food wrapper.

20. The process of claim 14 wherein the substrate is polyvinyl chloride.

* * * * *